United States Patent [19]
Joh et al.

[11] Patent Number: 4,508,535
[45] Date of Patent: Apr. 2, 1985

[54] CANNULA

[75] Inventors: Yasushi Joh; Noriaki Kaneko, both of Yokohama; Toshio Nagase, Houjōshinmachi, all of Japan

[73] Assignee: Nippon Zeon Co., Ltd., Tokyo, Japan

[21] Appl. No.: 483,138

[22] Filed: Apr. 8, 1983

[30] Foreign Application Priority Data

Apr. 10, 1982 [JP] Japan .................................. 57-59913
Apr. 10, 1982 [JP] Japan .................................. 57-59918

[51] Int. Cl.³ .......................................... A61M 25/00
[52] U.S. Cl. ..................................... 604/282; 604/174
[58] Field of Search ............... 604/280, 281, 282, 283, 604/4, 174, 175, 178

[56] References Cited

U.S. PATENT DOCUMENTS

| | | | |
|---|---|---|---|
| 2,211,975 | 8/1940 | Hendrickson | 604/282 |
| 3,903,895 | 9/1975 | Alley et al. | 604/178 |
| 4,117,836 | 10/1978 | Erikson | 604/281 X |
| 4,169,464 | 10/1979 | Obrez | 604/282 X |
| 4,173,981 | 11/1979 | Mortensen | 604/282 |
| 4,392,855 | 7/1983 | Oreopoulos | 604/175 |

Primary Examiner—Stephen C. Pellegrino
Attorney, Agent, or Firm—Armstrong, Nikaido, Marmelstein & Kubovcik

[57] ABSTRACT

The invention relates to a tubular cannula for use with an artificial heart in open heart surgery.

The cannula has a tubular portion with an axis having a three-dimensional configuration by being bent at least twice in different directions between an insertion distal end tip for insertion into a heart and a connection proximal end tip for connection with the artificial heart.

20 Claims, 14 Drawing Figures

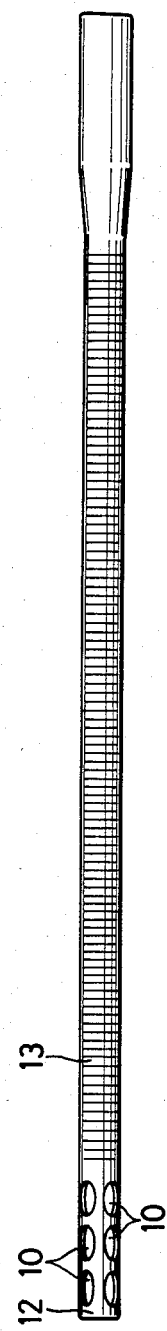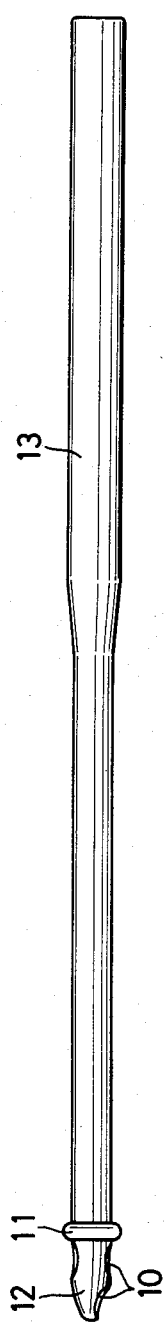

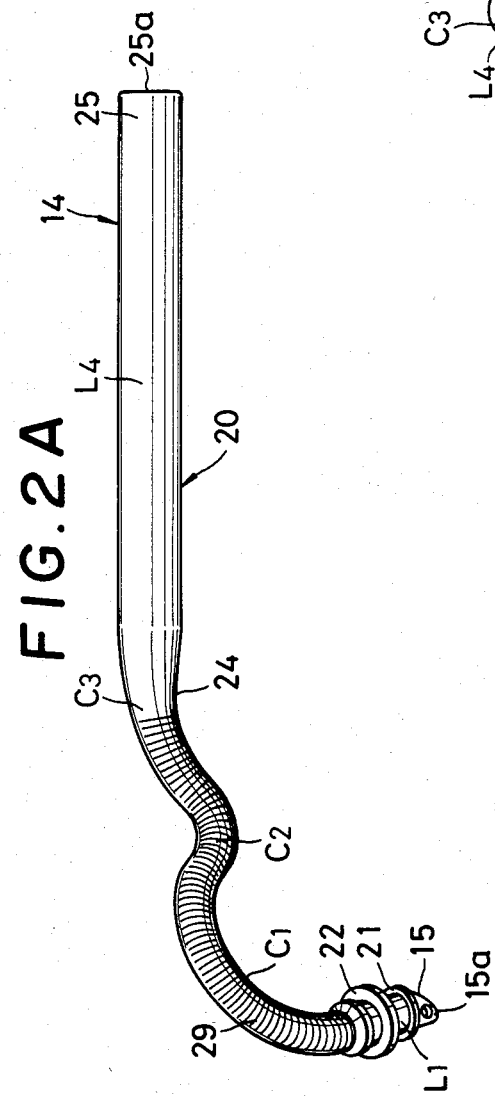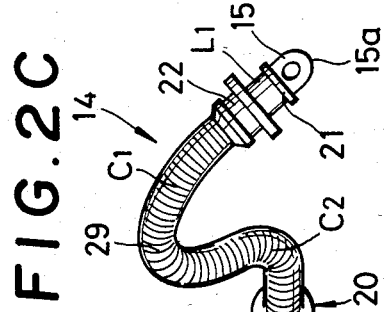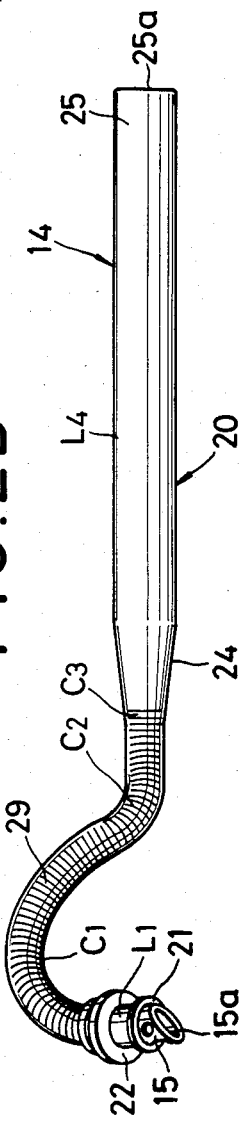

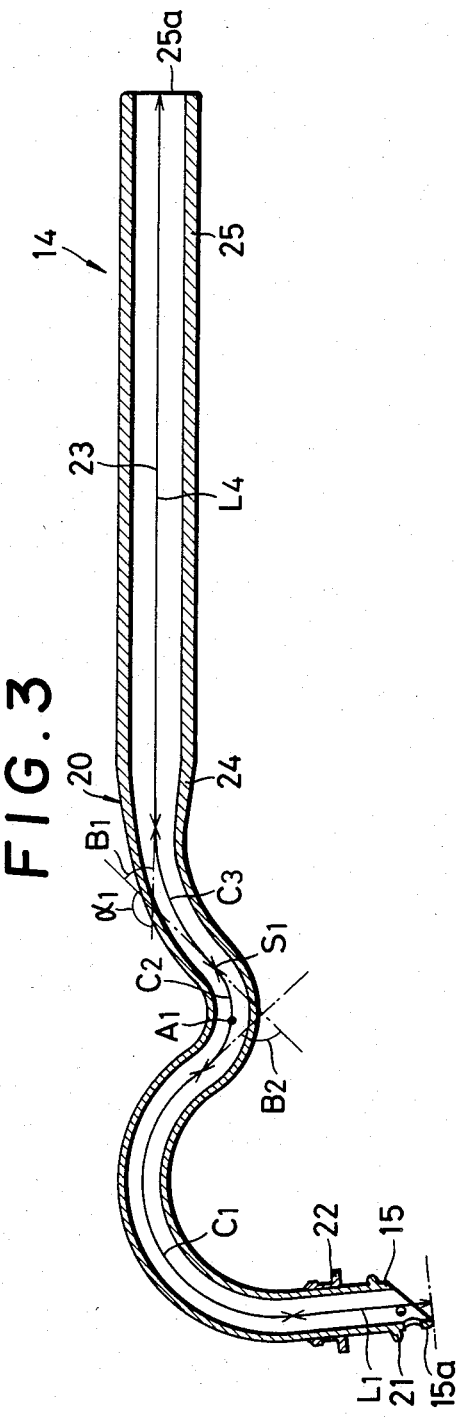

CANNULA

BACKGROUND OF THE INVENTION

1. Field of the Invention

The present invention relates to a novel cannula and, more particularly, to a cannula which may be suitably adapted for using as a ventricular assist device in heart surgery.

A cannula for heart-lung machine is conventionally used in open-heart surgery. However, the present invention provides a new type of cannula which has been developed for a total artificial heart or a partial or auxiliary artificial heart (to be simply referred to as an artificial heart hereinafter) for use in open-heart surgery based upon totally new technology.

2. Description of the Prior Art

With recent medical developments, the human life expectancy is becoming longer, however, the ratio of cardiac failure to all the various causes of death is also increasing. Artificial hearts are being developed for patients who suffer from serious heart diseases which are incurable by conventional operative techniques or medicine, such as chronic congestive heart failure, acute myocardial infarction, or postoperative low output syndrome. However, artificial hearts are still not commercially available. Moreover, only a few organizations or institutes are studying the subject, and only a little more than one hundred clinical tests have been reported. Meanwhile, the type of artificial heart under development is not limited to one, but various types thereof are being developed. Irrespective of type, any artificial heart, however, will require a novel cannula which in used to operate the artificial heart to assist, during or after the operation, the function of the natural heart of a patient suffering a serious heart problem until the patient's heart starts functioning normally by itself, thereby saving the patient's life.

FIGS. 1A and 1B show conventional tubular cannulae for an artificial heart-lung. Each of these cannulae has a small inner diameter, a straight axis, and openings 10 at an insertion or distal end 12. The cannula is flexible and may be bent two-dimensionally (e.g., into a U-shape). In the cannula shown in FIG. 1A, a metallic coil spring 13 is embedded inside except at a proximal end to be coupled to an artificial heart and at the insertion or distal end 12. In the cannula shown in FIG. 1B, a flange 11 is formed integrally with the cannula portion leading to the openings 10.

With the cannulas shown in FIGS. 1A and 1B, pressure loss is significant due to the small inner diameter, and the shape does not conform exactly to that of the heart, thus failing to allow full functioning of the artificial heart. Furthermore, when the straight cannula is as an inflow cannula, this cannula may press on the lung and prevent the movement of the patient's heart. Therefore, this type of cannula is not suitable as a cannula for an artificial heart. Further the cannula without the flange at the distal end portion as shown in FIG. 1A may become accidentally detached from the heart. In particular, when this type of cannula is used for an artificial heart, it may become more easily detached due to pulsation of the heart over a long time interval, thereby threatening the patient's life.

The first requirement of a cannula for allowing full functioning of an artificial heart lies on its shape. A patient's heart is located in the intrapleural space, i.e., the narrow space between side walls, and beats or pulsates vigorously. Cannulas are roughly classified into two types; an inflow cannula and an outflow cannula. An inflow cannula ejects blood from a left or right atrium, and guides the blood to the artificial heart. An outflow cannula guides blood from the artificial heart to the pulmonary artery or the aorta.

A cannula of either type must be capable of detouring the beating heart in order not to impose any restraint on the movement of the patient's heart, and must be as short as possible in order to reduce the pressure loss to the minimum. In order to satisfy these requirements, it is desired that the cannula has a special shape involving a special curvature or convolution. In addition, the bent portion of the cannula must not be pulsatile due to pulsation of the blood and must not cause the kinking phenomenon.

A cannula must also be able to be applied in various situations. For example, a cannula may be required to be used for males and females, adults and children, and so on. The heart of a patient suffering a heart problem is generally abnormally large, known as hypertrophy of the heart, and the degree of such hypertrophy differs from one individual to another. A cannula which may be used in such various situations has not yet been proposed. However, such a cannula is desired in order to satisfy practical needs.

Pulsation pressure from the human heart may be as high as 200 mmHg and pulsation frequency is 60 to 120 times per minute. A cannula must not allow peristaltic movement due to such pulsation. In a case where a cannula deforms in accordance with the pulsation of the artificial heart, the pulsation of the blood is absorbed by the cannula and the original functioning of the artificial heart is impaired. Accordingly, a cannula must not allow peristaltic deformation in any portion thereof due to blood pulsation during a heart operation.

If a cannula has a large diameter along its entire length, it exerts an excess pressure on the patient's heart to limit its functioning and therefore the artificial heart is reduced in its function of assisting the patient's heart. Thus, a cannula for an artificial heart preferably has a diameter smaller than a predetermined value, at least at that part thereof which directly contacts with the patient's heart. Conversely, the inner diameter of the connecting or proximal end of the cannula which is to be coupled to the artificial heart is preferably kept greater than a predetermined value. If the connecting end does not have a diameter greater than the predetermined value, pressure loss is caused before the blood from the artificial heart reaches the aorta or the pulmonary artery. A cannula must, finally, allow instant adjustment of its length during an operation. This is because the shape of the heart differs from one patient to another as has been mentioned earlier, and the cannula must be adjusted in length for each individual patient.

SUMMARY OF THE INVENTION

The present invention has been made in consideration of this and has for its object to provide a novel cannula and, more particularly, a cannula preferably used as an inflow cannula for an artificial heart. According to an aspect of the present invention, an inflow cannula of the present invention may be used for guiding blood ejected from the left atrium of a patient to the artificial heart. Blood which has reached the artificial heart is generally pulsated out of the artificial heart and is supplied to the ascending aorta through an outflow cannula. This technique is assumed to be most frequently adopted in a heart operation.

Although many heart surgery techniques employing the artificial hearts have been or are being developed by many surgeons, most operations are assumed to involve left heart assist of the patient's heart with an artificial heart. In order to guide the blood from the patient's heart to the artificial heart, blood is ejected from the left atrium of the patient's heart, and the ejected blood is guided to the artificial heart. According to the method which is most frequently adopted by heart surgeons, blood is ejected from the left atrium by inserting an inflow cannula into the left atrium from the rear portion of the patient's heart at the boundary between the pulmonary venous and the right atrium. In this case, the inflow cannula must have a shape such that it is capable of detouring toward the front side of the heart therealong and of preventing any pressure being applied to the heart.

According to a novel cannula of a special shape for meeting to such requirements as described above, the axis of the tubular portion extending from the connecting or proximal end to be coupled to an artificial heart to the insertion or distal end to be inserted into a patient's heart is bent at least twice in different directions, so that the overall cannula is bent three-dimensionally. As has been discussed hereinbefore, in order that an artificial heart may fully function, a cannula must be as short as possible and must not interfere with the movement of the patient's heart when it is inserted into a desired portion of the left atrium. For this purpose, the cannula must have the shape as described above. When a cannula having such a shape is used, part or all of the functioning of the patient's heart may be effectively assist by the artificial heart.

The above, and other objects, features and advantages of the invention, will be apparent in the following detailed description of illustrative embodiments of the invention which is to be read in connection with the accompanying drawings wherein the same reference numerals are used to identify the same parts in the several views.

BRIEF DESCRIPTION OF THE DRAWINGS

FIGS. 1A and 1B are plan views of a conventional cannula which is used for an artificial heart-lung;

FIGS. 2A, 2B and 2C are a plan view, a front view and a left side view, respectively, of a cannula according to an embodiment of the present invention;

FIG. 3 is a longitudinally sectional, two-dimensionally developed view of the cannula shown in FIGS. 2A to 2C;

FIG. 4 is a two-dimensionally developed representation of the axis of the tubular portion of the cannula shown in FIGS. 2A to 2C;

DETAILED DESCRIPTION OF THE PREFERRED EMBODIMENTS

Figure 5:
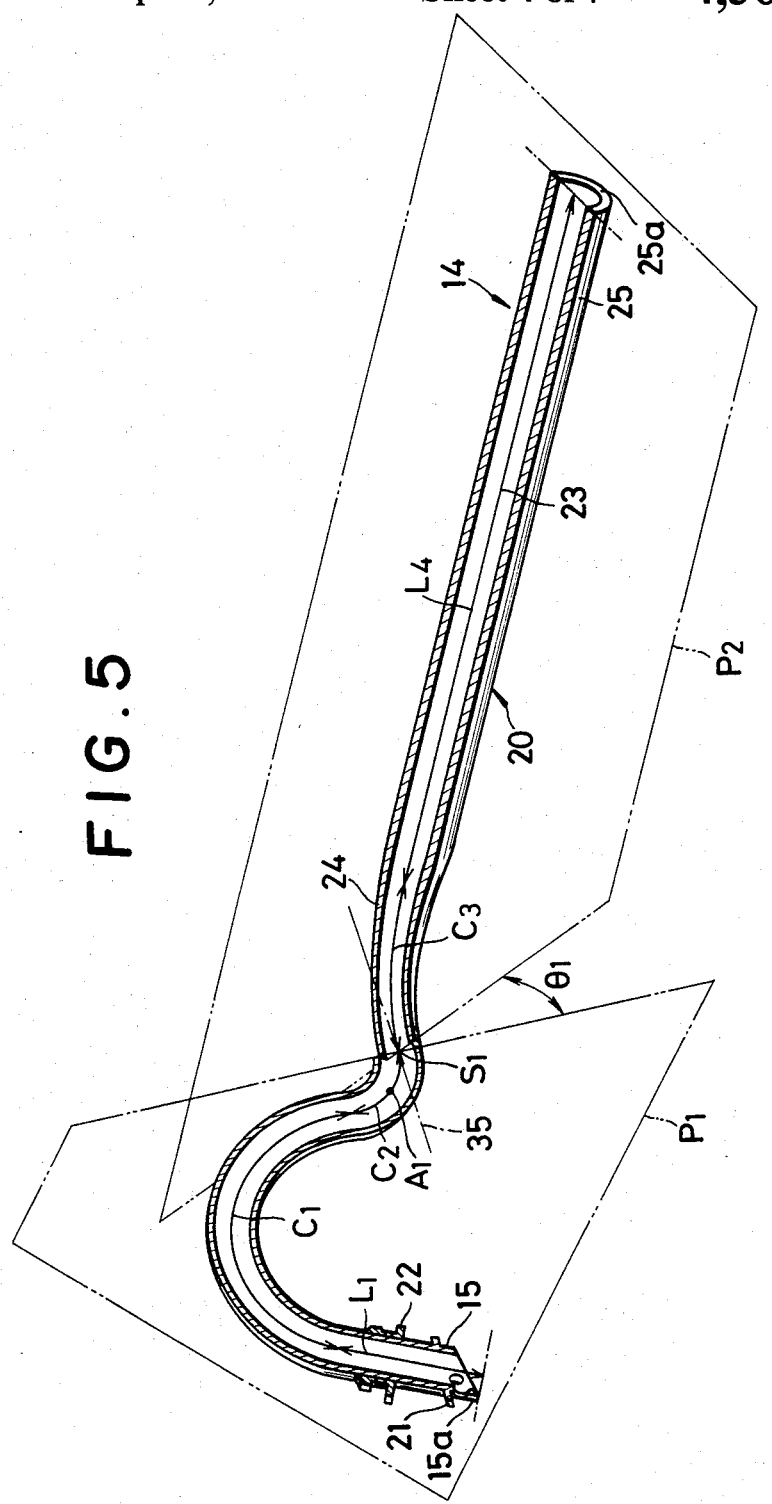
FIG. 5 is a longitudinally sectional view of the cannula shown in FIGS. 2A to 2C along two different imaginary planes.

A cannula according to an embodiment of the present invention has a three-dimensionally bent specific shape as shown in FIGS. 2A to 2C, 3 and 5. As shown in FIGS. 6A and 6B, a cannula 14 is used for blood ejection when its insertion or distal end 15 is inserted into a left atrium 17 of a patient's heart 16. Referring to FIGS. 3 and 4, a tubular portion 20 of this cannula 14 has a bent portion $C_1$ extending from the insertion end 15 so as to detour the right atrium, a bent portion $C_3$ extending along a right ventricle 18 toward the artificial heart through the split opening between sternum, and a supplementary bent portion $C_2$.

According to the present invention, the bent shape of the cannula is important; it must be bent in a three-dimensional configuration with no stress acting on it such that an axis 23 of the tubular portion 20 is bent at least twice in two different directions. If the degree of bending or the radius of curvature, especially, of the bent portion $C_1$ is not proper, various problems will arise. Thus, if the radius of curvature is too great, an excess pressure acts upon the heart. On the other hand, if the radius of curvature is too small, too much force acts on the insertion end 15 of the cannula which is coupled to the patient's heart, and it may become accidentally detached therefrom. In addition, an excess pressure may act upon the lung.

As may be seen from the two-dimensionally developed view shown in FIG. 3, the cannula 14 comprises the tubular portion 20 whose axis 23 is three-dimensionally bent with no force acting thereon and which has a seamless and continuously curved inner surface, a flange 21 which is formed integrally with the insertion end 15 of the tubular portion 20, and a flanged cylindrical holding member 22 slidably fitted around the tubular portion 20 in the vicinity of the flange 21. The axis 23 of the tubular portion 20 has three bent portions $C_1$, $C_2$ and $C_3$, (having, for example, a circular arc shape) such that the overall axis 23 is continuous and does not form a pointed portion between the bent portions. The bent portions $C_2$ and $C_3$ form an overall S-shape, while the bent portions $C_1$ and $C_2$ form an inverted S-shape. Accordingly, the combination of the bent portions $C_1$ to $C_3$ makes a meandering configuration or convolution. The bent portion $C_1$ terminates into a straight portion $L_1$, and the bent portion $C_3$ terminates into a straight portion $L_4$.

Figure 6A:
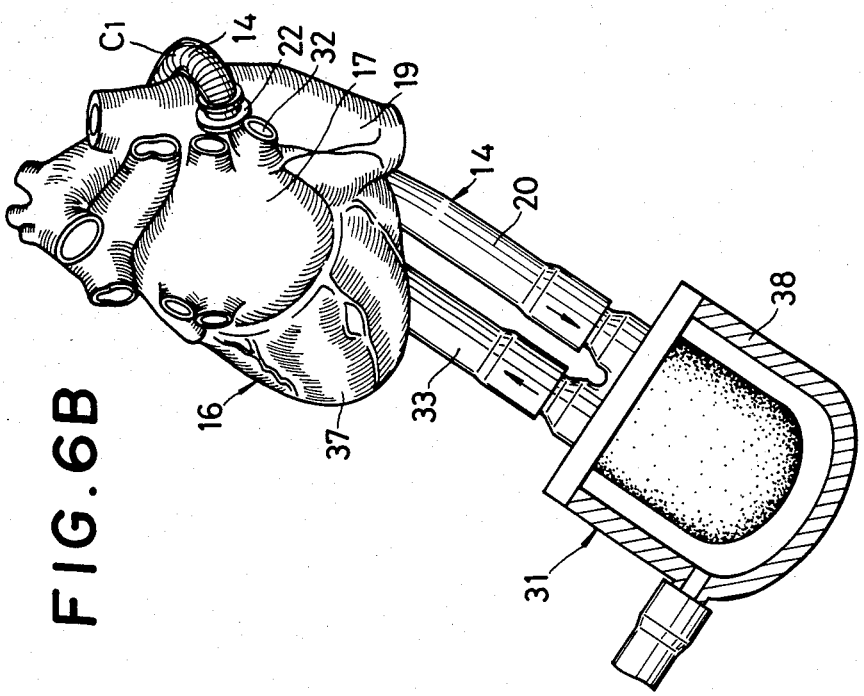
FIG. 6A is a view showing the cannula shown in FIGS. 2A to 2C as used for an ejection cannula for a human heart as viewed from its front side.
Figure 6B:
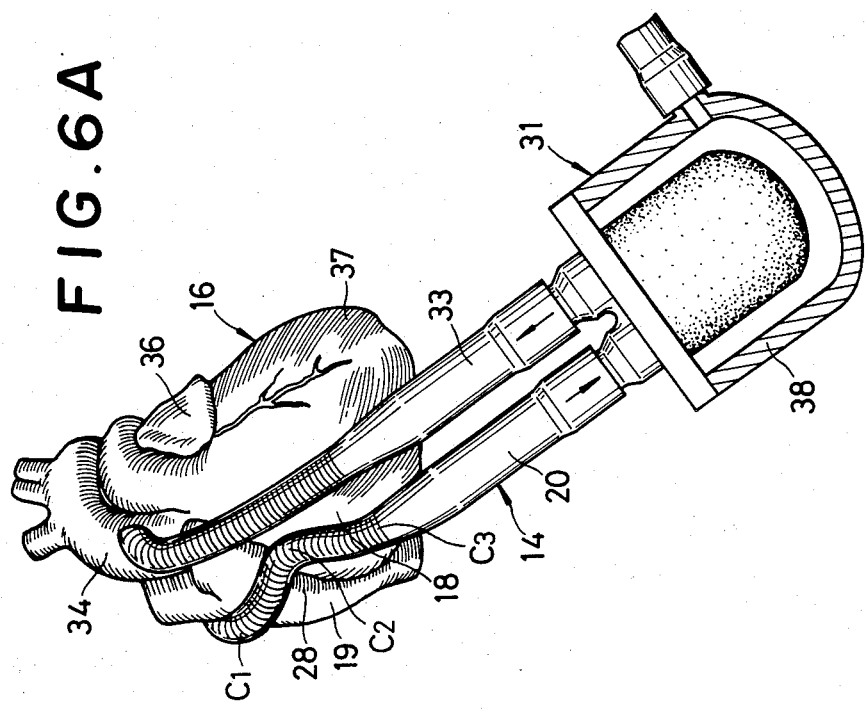
FIG. 6B is a rear side view of the same.

As may be seen from FIG. 5, the axis 23 at the straight portion $L_1$ and the bent portions $C_1$ and $C_2$ is located within a first imaginary plane $P_1$, and the axis 23 at the bent portions $C_3$ and the straight portion $L_4$ is located within a second imaginary plane $P_2$. The first and second imaginary planes $P_1$ and $P_2$ form an angle $\theta_1$. In other words, when the bent portions $C_1$ and $C_2$ and the straight portion $L_1$ of the two-dimensionally developed cannula 14 shown in FIG. 3 are pivoted through the angle $\theta_1$ in a predetermined direction about a rotating axis 35 defined by a tangent, with respect to the axis 23, at a connecting point $S_1$ between the portions of the axis 23 corresponding to the bent portions $C_2$ and $C_3$, respectively, a cannula as shown in FIGS. 2A to 2C and 5 is obtained wherein the axis 23 is bent three-dimensionally. The angle $\theta_1$ is preferably within the range of 5° to 180° and more preferably within the range of 10° to 85°. The straight portion $L_1$, the bent portions $C_1$ and $C_2$ and part of the bent portion $C_3$ of the tubular portion 20 of the cannula 14 have a small diameter to constitute a small diameter portion. Most of the straight portion $L_4$ has a large diameter to constitute a large diameter portion. The bent portion $C_3$ and, if necessary, the straight portion $L_4$ constitute a connecting portion 24 whose diameter gradually tapers to connect the small and large diameter portions together. The length of the connecting portion 24 is preferably within the range of 8 to 200 mm and more preferably within the range of 10 to 50 mm.

In principle, the cannula 14 may further have straight portions $L_2$ and $L_3$ of suitable lengths between the bent portions $C_1$ and $C_2$ and the bent portions $C_2$ and $C_3$, respectively, as shown in FIG. 4. In a description to follow, the cannula 14 shown in FIGS. 2A to 2C, 3 and 5 will be described with reference to the representation shown in FIG. 4. An angle $\alpha_1$ formed by the axes of the straight portions $L_3$ and $L_4$ (i.e., the angle formed by the tangent at one end of the axis 23 of the bent portion $C_3$ and a tangent at the other end thereof) is preferably within the range of 60° to 160°. Therefore, an angle $\beta_1$ through which the bent portion $C_3$ bends the axis 23 of the tubular portion 20 is preferably within the range of 20° to 120°. This is because the important features of the present invention are the radius of curvature of the bent portion $C_1$ which is to extend from the insertion end 15 of the tubular portion 20 so as to detour the outside of a right atrium 19, and also the radii of curvature of the bent portions $C_2$ and $C_3$ which are to extend along the right atrium 19 through the intrapleural space to the front side of the heart and then between the interspace of the sternum. The straight portion $L_4$ of the tubular portion 20 between the bent portion $C_3$ and a proximal end tip 25a has a large diameter so as to prevent pressure loss. The proximal end tip 25a is coupled to a blood inlet port of the artificial heart. The bent angle of the bent portion $C_3$ is preferably within the range of 20° to 120° as has been described above in order to allow connection to an artificial heart 31 within a minimum distance. If this angle falls outside this range, the length of the tubular portion 20 becomes too great, resulting in excessive pressure loss and insufficient blood ejection.

The axis 23 at the bent portion $C_1$ is arcuated and may comprise one or a combination of a plurality of continuous curves having a radius of curvature of 10 to 90R (nR in this connection means an arc of a circle having a radius of n mm). The curved length of the tubular portion 20 of the cannula 14 from an insertion end tip 15a to a middle point $A_1$ of the bent portion $C_2$ is preferably within the range of 45 to 250 mm. If the radius of curvature nR described above is smaller than 10R, it is too small even for an infant. Then, the cannula 14 presses against the patient's heart too much, interfering with its beating, thus preventing early recovery of normal functioning of the heart. When the radius of curvature is greater than 90R, an abnormal force acts upon the insertion end 15 of the cannula 14, so that the insertion end 15 may inadvertently become detached from the left atrium 17 or an excessive pressure may act upon the lung. When the curved length described above is smaller than 45 mm, a sufficient bent portion for detouring around the right atrium may not be obtained. Then, an excessive pressure acts upon the patient's heart, similarly preventing early recovery of normal functioning of the heart. On the other hand, if the curved length is greater than 250 mm, the bent portion for detouring around the right atrium becomes too long. Then, an excessive pressure may act upon the lung or the insertion end 15 may become detached from the heart due to the elasticity of the cannula 14.

As has been described above, the radius of curvature of the axis of the bent portion $C_1$ is preferably within the range of 10 to 90R. However, the radius of curvature of the axis of next bent portion $C_2$ may be smaller than that of the bent portion $C_3$. After detouring around the right atrium 19, the cannula must then be extended along a right ventricle 18 toward the bulged portion at the front side of the heart. For this purpose, the bent portion $C_2$ preferably has a small radius of curvature. In general, in order that the cannula extend along the right ventricle 18 below a right auricle 28 of the heart, the radius of curvature of the axis of the bent portion $C_2$ is preferably within the range of 5 to 30R. The bent portion $C_2$ may comprise first and second bent portions with a straight portion interposed therebetween. In this case, the radius of curvature of the axis of the first bent portion next to the bent portion $C_1$ may be equal to or greater than that of the second bent portion. However, the radii of curvature of the first and second portions are preferably smaller than that of the bent portion $C_1$. When the radius of curvature of the axis of the bent portion $C_2$ is smaller than 5R, the cannula is bent too much at this portion. Then, blood does not flow smoothly and forms a vortex, causing undesirable effects such as hemolysis or coagulation. On the other hand, when the radius of curvature of the axis of the bent portion $C_2$ is greater than 30R, the cannula detours too far, resulting in too long a cannula and too great a pressure loss. For the same reason, the inner diameter of the small diameter portion of the cannula from the insertion end 15 to the part detouring the right atrium is preferably within the range of 3 to 15 mm. The inner diameter of the large diameter portion of the cannula from the portion extending outside the patient's body to the coupling portion with the artificial heart is preferably within the range of 8 to 25 mm. When the inner diameter of the small diameter portion is smaller than 3 mm, too great a pressure loss is caused. When the inner diameter of the small diameter portion exceeds 15 mm, an excessive pressure acts upon the patient's heart. In order to minimize the pressure loss, the inner diameter of the large diameter portion is preferably larger than 8 mm. However, when the inner diameter of the large diameter portion exceeds 25 mm, a connector of the different diameter is required. This results in a stagnation of blood flow and is not, therefore, desirable.

The thickness of the small diameter portion is preferably within the range of 0.2 to 5 mm, while that of the large diameter portion is preferably 1.2 to 7 mm. The length of the straight portion $L_2$ may be 0 to 500 mm, that of the straight portion $L_3$ may be 0 to 100 mm, and that of the straight portion $L_4$ may be 0 to 100 mm. In the embodiment shown in FIGS. 2A to 2C, $L_2=0$ mm, $L_3=0$ mm, and $L_4=30$ mm, respectively.

In the cannula of the present invention, the ratio of the length of the small diameter portion convolutely extending along the right atrium to that of the large diameter portion is preferably within the range of 1:1 to 1:10. When the ratio falls outside this range, operability of the cannula is degraded. In the cannula of the present invention, the small diameter portion of a relatively small diameter and of a curved shape and the large diameter portion at the side to be coupled to the artificial heart are integrally formed with each other through the connecting portion 24 described above such that at least the inner surface of said tubular portion 20 is a seamless and smooth surface without any corners. The small and large diameter portions of the tubular portion 20 have a thickness which falls within a predetermined range in order to prevent deformation due to blood pulsation or kinking. In particular, the small diameter portion is reinforced by embedding therein a metallic coil spring or spiral body 29.

The flange 21 formed around the insertion end 15 is preferably inclined such that it forms an angle of 30° to 80° with respect to the axis 23 of the tubular portion 20, as shown in FIG. 3. When this angle falls outside this range, it does not fit well with a heart wall or a blood vessel wall and the insertion end 15 is inserted only insecurely. This tends to cause stagnation of blood flow or formation of a thrombus. Since a human heart is a collective body of spherical surfaces, the above-mentioned angle is preferably within the range of 50° to 75° from the anatomical viewpoint. The width of the flange 21 extending from the tubular portion 20 is preferably within the range of 1 to 5 mm. If the width is below 1 mm, the effect of the flange 21 in securely fixing the insertion end 15 and preventing formation of a thrombus is decreased. However, when the width is greater than 5 mm, the cut portion of the heart for allowing insertion of the insertion end 15 becomes too large. This means unnecessary damage to the cardiac muscular tissue or blood vessel wall. The shape of the flange 21 may be freely selected in accordance with applications or the shape of the heart or the portion of the heart for receiving the cannula insertion end. The shape of the flange 21 need only allow a good fit with the heart wall or blood vessel wall. Presence of the flange 21 is not always necessary. Cannulation can be made without the flange 21, however, in this case, another means to fix the cannulation should be adopted.

Figure 7A:
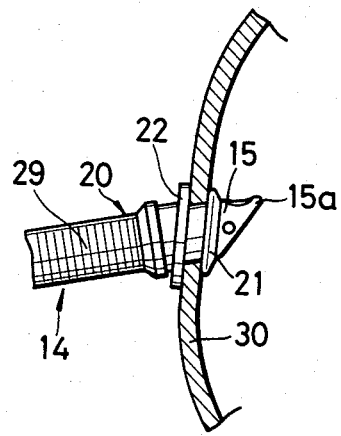
FIG. 7A is a sectional view showing the state wherein the distal end of the cannula shown in FIGS. 2A to 2C is inserted into the human heart.
Figure 7B:
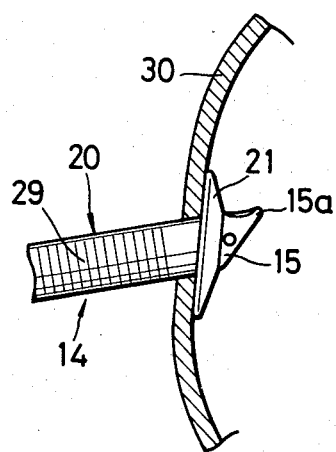
FIGS. 7B and 7C are sectional views showing modifications of that shown in FIG. 7A, respectively.
Figure 7C:
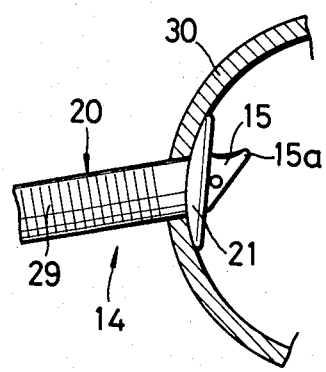

FIG. 7A shows a state wherein the insertion end 15 of the cannula 14 shown in FIGS. 2A to 2C is inserted into a heart wall 30. As may be seen from FIG. 7A, the flange 21 formed around the insertion end 15 of the cannula 14 fits tightly with the inner surface of a heart wall 30. The heart wall 30 may be clamped between the flange 21 and the holding member 22, which may be omitted if not necessary. When this holding member is omitted, the cannula has only flange 21 at its end portion. When the flange 21 is also omitted, the cannula is just tubular to its end. Considering blood flow, the flange 21 may be of frustoconical shape such that its surface at the side of the insertion end tip 15a is tapered, as shown in FIG. 7B. In contrast to this, for an application for a heart of an infant having a small radius of curvature, the surface of the flange 21 at the side of the insertion end tip 15a may be flat and the other surface may be tapered as shown in FIG. 7C. In any case, the inner surface of the heart wall 30 and the flange 21 preferably fit tightly with each other after insertion of the insertion end 15 into the heart. The cannula's tip in FIGS. 7B and 7C may not have the flange 21, however, in this case another means to fix the cannulation is necessary.

The material of the cannula of the present invention may be polyurethane or polyvinyl chloride containing a plasticizer. Examples of polyurethane may be a known polyester-type polyurethane or a polyether-type polyurethane. When such a polyurethane is used, it may be crosslinked for good mechanical strength. A polyester-type polyurethane is suitable for producing an elastomer with high elasticity, great tensile strength and hardness, and may, therefore, be conveniently used for the cannula of the present invention.

The amount of a crosslinking agent to be added is preferably within the range of 0.01 to 5% by weight based on the weight of the total polyurethane component. A plasticizer for polyvinyl chloride may be a known plasticizer for polyvinyl chloride, such as dioctyl phthalate or dioctyl adipate. In this case, soft polyvinyl chloride may comprise a so-called polyvinyl chloride paste consisting of polyvinyl chloride and a plasticizer. The amount of the plasticizer is preferably within the range of 40 to 100% by weight and more preferably within the range of 50 to 80% by weight based on the polyvinyl chloride used. The polyvinyl chloride may contain a known stabilizer such as a nontoxic calcium-zinc organic complex or the like. The degree of polymerization of the polyvinyl chloride is preferably within the range of 500 to 2,000. In order to improve performance in preventing a thrombus, the cannula of the present invention may be coated on its inner surface with an anticoagulant for improving compatibility with blood. An anticoagulant may be conveniently used which consists of polyurethane and polydialkylsiloxane, at least polydialkylsiloxane being crosslinked.

The cannula 14 of one embodiment of the present invention shown in FIGS. 2A to 2C, 3 and 5 will now be described in more detail. The material of a cannula 14 is polyvinyl chloride containing a plasticizer. The plasticizer is dioctyl phthalate which is used in the amount of 70% by weight based on the weight of the polyvinyl chloride. The cannula 14 has a first bent portion $C_1$ convolutely extending from next to an insertion end 15 and detouring around the right atrium 19, a third bent portion $C_2$ extending from the first bent portion $C_1$ and running apart from the heart directing to the split chink of the sternum, and a second bent portion $C_3$ extending from the third bent portion $C_2$ and locating in the vicinity of the split opening between sternum. Since the imaginary plane involving the second bent portion $C_3$ and another imaginary plane involving the bent portions $C_1$ and $C_2$ cross (or stagger), the overall tubular portion 20 of the cannula 14 is bent three-dimensionally. The inner diameter of the small diameter portion of the tubular portion 20 is 10 mm. An annular flange 21 is integrally formed with an insertion end 15 for facilitating fixing of the inserted portion of the cannula into the heart. In order to obtain good shape retention capacity and to prevent kinking, a metallic coil spring 29 is embedded from a position about 2 cm away from the flange 21 on the opposite side to the insertion end tip 15a, to the proximal end of the small diameter portion. The small diameter portion of the tube extending from the insertion end tip 15a to the portion protected by the metallic coil spring 29 has a thickness of 1 mm. The large diameter portion constituting most of the straight portion $L_4$ has a thickness of 2.5 mm. The connecting portion 24 between these two tube portions has a thickness of 1 mm at the connecting point with the small diameter portion and has a thickness of 2.5 mm at the connecting point with the large diameter portion. The thickness of the connecting portion 24 changes proportionally from one end to the other end. The inner diameter of the large diameter portion is 15 mm.

The axis of the first bent portion $C_1$ has a radius of curvature of 30 to 40R. The curved length of the axis extending from the insertion end tip 15a to the middle point $A_1$ of the third bent portion $C_2$ is 100 mm. The axis of the third bent portion $C_2$ has a radius of curvature of 10R and bends the axis 23 of the tubular portion 20 through an angle $\beta_2$ of 53°. The second bent portion $C_3$ bends the axis 23 of the tubular portion 20 through an angle $\beta_1$ of 70°. The angle $\theta_1$ formed by an imaginary plane $P_1$ including the axes of the bent portion $C_3$ and the straight portion $L_4$, and an imaginary plane $P_2$ including the axes of the bent portions $C_1$, is 30°. The flange 21 has two surfaces which are substantially flat and is inclined to form an angle of 60° with respect to the axis 23 of the tubular portion 20.

FIGS. 6A and 6B show a state wherein the cannula 14 as shown in FIGS. 2A to 2C is used as an inflow cannula for an auxiliary artificial heart 31 of the sack-type for assisting the function of the left ventricle 37. Referring to FIGS. 6A and 6B, the inflow cannula 14 is inserted into the left atrium 17 from the boundary between a pulmonary venous 32 and the right atrium 19 on the rear side of the heart 16. An outflow cannula 33 of which only the insertion end is curved is inserted toward the ascending aorta 34. In this embodiment, a pneumatic sack-type pump 35 is used as the pump for the partial or auxiliary artificial heart 31. When the auxiliary artificial heart 31 is used in heart operation, it is considered best to insert an inflow cannula from the rear side of the heart 16 to the left atrium 17, as in this embodiment, in order to perform blood ejection through a narrow space between the heart side walls without interfering with the movement of the patient's heart. This may be achieved only with the cannula of the present invention which has not been available heretofore.

A modification of the cannula shown in FIGS. 2A to 2C will now be described. The cannula of this modification differs from the cannula shown in FIGS. 2A to 2C in the following respects. One end of the metallic coil spring 29 extends to the position of the flange 21, and the other end thereof extends to a part of the large diameter portion. The radius of curvature of the axis 23 of the first bent portion $C_1$ is 42R, and that of the third bent portion $C_2$ is 15R. The angle $\beta_2$ through which the bent portion $C_2$ bends the axis 23 of the tubular portion 20 is 54°. The small diameter portion has an inner diameter of 9 mm and a thickness of 0.6 mm. The large diameter portion has an inner diameter of 12 mm and a thickness of 2.0 mm. The remaining details of the cannula of this modification remain the same as those of the cannula shown in FIGS. 2A to 2C. Thus, the tubular portion of the cannula of this modification has a shape such that its axis has three-dimensional configuration, and the inner surface thereof is seamless.

The cannula of this modification comprises a polyvinyl chloride composition containing 80% by weight of the dioctyl phthalate based on the weight of polyvinyl chloride. A similar cannula may be obtained from a polyurethane. The cannula of this modification may also be used in a manner as shown in FIGS. 6A and 6B.

Figure 8:
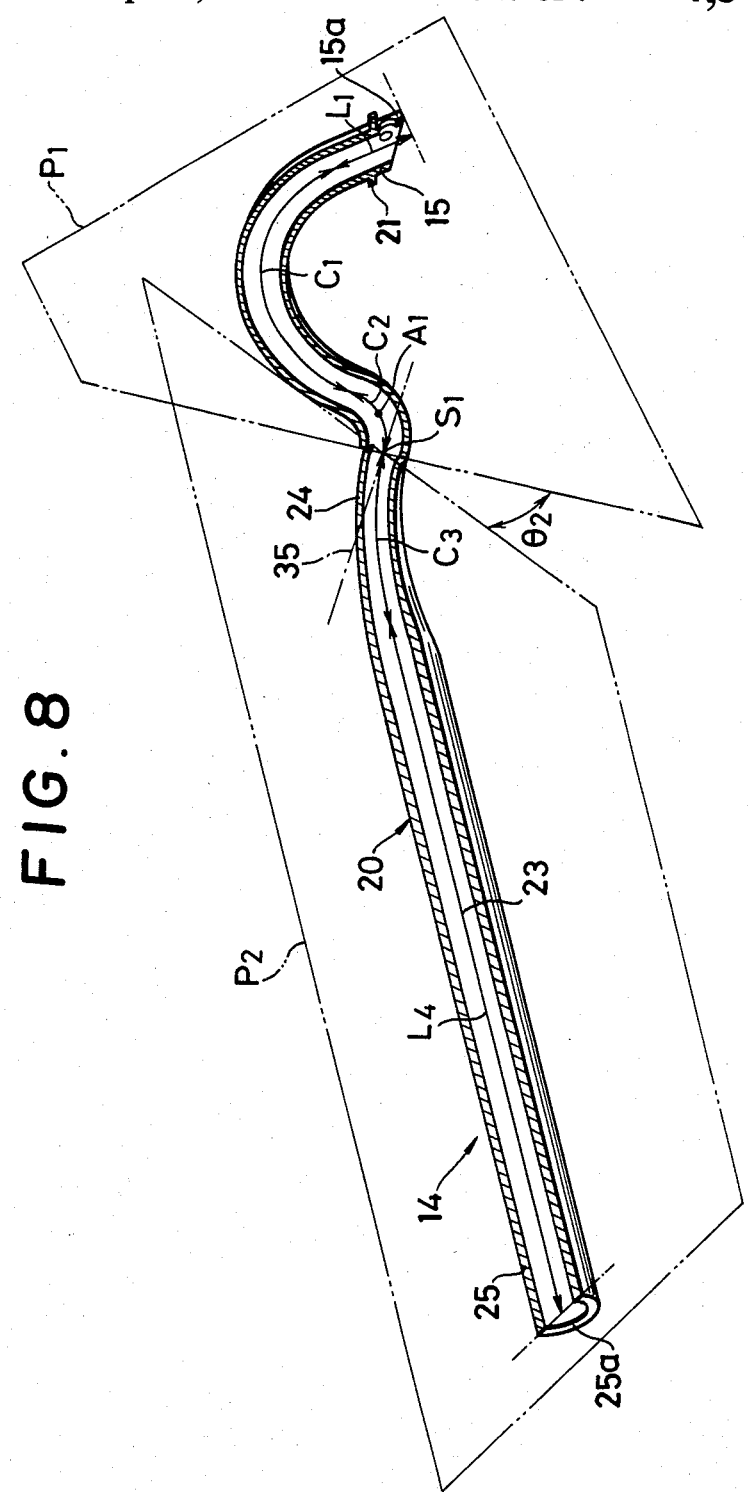
FIG. 8 is a longitudinally sectional view of a cannula according to another embodiment of the present invention along two different imaginary planes.

FIG. 8 shows another embodiment of the present invention. The cannula of this embodiment is for ejection of blood from a left auricle 36. An insertion end 15 detours around a left ventricle 37 from the front side of a patient's heart 16 and is inserted into a left atrium 17 from the left auricle 36.

The cannula shown in FIGS. 2A to 2C and 5 detours around the right atrium, while that shown in FIG. 8 detours around the left atrium. As may be seen from a comparison of FIGS. 5 and 8, the imaginary plane $P_2$ is pivoted about the rotating axis 35 through the angle $\theta_2$ with respect to the imaginary plane $P_1$ in the cannula shown in FIG. 8, but in the opposite direction to that of the cannula shown in FIG. 5. Except in this point, the cannula shown in FIG. 8 has basically the similar shape as that of the cannula shown in FIG. 5. Therefore, a two-dimensionally developed view of the cannula shown in FIG. 8 will be similar to that shown in FIG. 4. Thus, the cannula shown in FIG. 8 has a bent portion $C_1$ for allowing the insertion end 15 to detour from the left atrium 17 to the left ventricle 37, a bent portion $C_2$ bent in the opposite direction to that of the bent portion $C_1$ to extend from the left ventricle 37 through a space between sterna, and a bent portion $C_3$ bent in a direction different from those of the bent portions $C_1$ and $C_2$ at the position where the cannula extends outside the body of the patient through the space between sternal ribs. The three bent portions $C_1$ to $C_3$ are continuously connected to the straight portion $L_4$ comprising the large diameter portion with a seamless inner surface, thereby providing a three-dimensionally bent cannula.

A particular example of the cannula shown in FIG. 8 is as follows. The radius of curvature of the bent portion $C_1$ is 30R, that of the bent portion $C_2$ is 12R, and the angle $\beta_1$ through which the bent portion $C_3$ bends the axis 23 of the tubular portion 20 is 70°. The angle $\theta_2$ between the imaginary plane $P_1$ including the axis of the bent portion $C_3$ and the straight portion $L_4$, and the imaginary plane $P_2$ including the axis of the bent portions $C_1$ and $C_2$, is 30°. The cannula of this embodiment comprises a polyvinyl chloride composition containing a plasticizer. The plasticizer is dioctyl phthalate which is used in the amount of 70% by weight based on the weight of the polyvinyl chloride. The inner diameter of the three-dimensionally bent small diameter portion is 11 mm. An annular flange 21 is formed at the insertion end 15 of the cannula so as to facilitate fixing of the insertion end 15. In order to maintain good shape retention capacity and to prevent kinking, a metallic spiral body or coil spring 29 is embedded from a position at about 1.0 cm away from the flange 21 on the opposite side to the insertion end tip 15a, to the proximal end of the small diameter portion. The thickness of the small diameter portion extending from the insertion end tip 15a and including the part protected by the metallic coil spring 29 is 1.1 mm. The large diameter portion not protected by the metallic coil spring 29 and extending to a proximal end tip 25a has a thickness of 2.2 mm and an inner diameter of 14 mm. The flange 21 of this embodiment may be one similar to that shown in FIGS. 2A to 2C.

When the cannulas shown in FIGS. 2A to 2C and 5 and in FIG. 8 were used as inflow cannulas to assist the function of left ventricle of a goat using a sack-type auxiliary artificial heart 31 as shown in FIGS. 6A and 6B, both could be easily inserted. After two weeks, no disengagement from the heart or excessive pressure acting upon the heart was observed. The cannulas were thus used conveniently and did not cause the formation of thrombus inside the tube.

Although illustrative embodiments of the invention have been described in detail herein with reference to the accompanying drawings, it is to be understood that the invention is not limited to such precise embodiments, and that various changes and modifications may be effected therein by one skilled in the art without departing from the scope or spirit of the invention as defined in the appended claims.

What is claimed is:

1. A tubular cannula for use as connected to an artificial heart compensating for partial or entire functioning of a heart function, wherein an axis of a tubular portion of said cannula has a three-dimensional configuration by being bent at least twice in different directions between an insertion distal end tip for insertion into a heart and a connection proximal end tip for connection with the artificial heart, said tubular portion comprising a first bent portion of an arcuated shape, located in the vicinity of said insertion distal end tip; a second bent portion of an arcuated shape located between said first bent portion and said connection proximal end tip; and a third bent portion of an arcuate shape, located between said first bent portion and said second bent portion; wherein an angle is formed by a first imaginary plane including an axis of said first bent portion and a second imaginary plane including an axis of said second bent portion, said angle being within a range of 5° to 85° and preferably within a range of 10° to 45°, and wherein, said third and second bent portions form an overall S-shape, and said first and third bent portions form an overall inverted S-shape, such that the combination of said first through third bent portions forms a meandering configuration.

2. A cannula according to claim 1, wherein an angle through which said axis of said tubular portion is deflected by said second bent portion is 20° to 120°.

3. A cannula according to claim 1, wherein said axis of said first bent portion has a radius of curvature of 10 to 90R.

4. A cannula according to claim 1, wherein a curved length of said axis between said insertion distal end tip and a middle point of said third bent portion is 45 to 250 mm.

5. A cannula according to claim 1, wherein a radius of curvature of an axis of said third bent portion is smaller than a radius of curvature of said axis of said first bent portion.

6. A cannula according to claim 4, wherein a radius of curvature of said axis of said third bent portion is 5 to 30R.

7. A cannula according to claim 1, wherein said axis of said third bent portion is included in said first imaginary plane.

8. A cannula according to claim 1, wherein said tubular portion further includes a first straight portion contiguous with a distal end side of said first bent portion.

9. A cannula according to claim 8, wherein said axis of said first straight portion is included in said first imaginary plane and extends to said insertion distal end tip.

10. A cannula according to claim 8, wherein said tubular portion further includes a second straight portion which is contiguous with a proximal end side of said second bent portion and which extends to said connection proximal end tip.

11. A cannula according to claim 10, wherein an axis of said second straight portion is included in said second imaginary plane.

12. A cannula according to claim 1, wherein a flange protrudes from an outer surface of an insertion end of said tubular portion, and said flange is inclined with respect to said insertion end to form an angle of 30 to 80° with respect to said axis of said tubular portion.

13. A cannula according to claim 12, wherein said flange protrudes for a distance of 1 to 5 mm.

14. A cannula according to claim 12, wherein a flanged cylindrical holding member is slidably fitted around said insertion end of said tubular portion on a side of said flange 21 opposite to said insertion distal end tip.

15. A cannula according to claim 1, wherein said tubular portion has a small diameter portion extending from said insertion distal end tip through said first bent portion, and a large diameter portion connected to said small diameter portion through a connecting portion and extending to said connection proximal end tip, said large diameter portion having an inner diameter larger than an inner diameter of said small diameter portion, and at least an inner surface of said tubular portion being a seamless and smooth surface without any corners.

16. A cannula according to claim 15, wherein said tubular portion further includes a straight portion which is contiguous with a proximal end side of said second bent portion and extends to said connection proximal end tip, an axis of said straight portion is included in said second imaginary plane, and a part or entirety of said straight portion is included in said large diameter portion.

17. A cannula according to claim 15, wherein one end of said connection portion has an inner diameter substantially equal to the inner diameter of said small diameter portion connected thereto, and the other end of said connection portion has an inner diameter substantially equal to the inner diameter of said large diameter portion connected thereto, an inner diameter of said connection portion gradually increasing from one end to the other end.

18. A cannula according to claim 17 wherein said small diameter portion has the inner diameter of 3 to 15 mm and a thickness of 0.2 to 5 mm, said large diameter portion has the inner diameter of 8 to 25 mm and a thickness of 1.2 to 7 mm, and a ratio of a length of said small diameter portion to a length of said large diameter portion is 1:1 to 1:10.

19. A cannula according to claim 17, wherein said connecting portion has a length of 8 to 200 mm and preferably 10 to 50 mm.

20. A cannula according to claim 1, wherein a metallic spiral reinforcement body is embedded in said tubular portion in a suitable portion excluding the vicinity of said insertion distal end tip.

* * * * *